United States Patent [19]

De Munck et al.

[11] Patent Number: 5,130,107
[45] Date of Patent: Jul. 14, 1992

[54] MINIMIZING COBALT CATALYST LOSS IN THE PRODUCTION OF ALCOHOLS BY HYDROFORMYLATION OF OLEFINS

[75] Inventors: Nicolaas A. De Munck, Barendrect; Mattheus D. Olijve, Spykeisse, both of United Kingdom; Raf Caers, Edegem, Belgium; Arie Van Vliet, Bondues, France; Jean A. A. Hanin, Rixensart; Eddy Van Driessche, Eekloo, both of Belgium

[73] Assignee: Exxon Chemical Patents Inc., Linden, N.J.

[21] Appl. No.: 632,037

[22] Filed: Dec. 21, 1990

Related U.S. Application Data

[63] Continuation-in-part of Ser. No. 447,881, Dec. 8, 1989, abandoned.

[30] Foreign Application Priority Data

Dec. 8, 1988 [GB] United Kingdom ............... 8828695

[51] Int. Cl.$^5$ ............................................. C01G 51/06
[52] U.S. Cl. .................................... 423/144; 423/140; 423/417; 423/419 R; 568/451; 568/909
[58] Field of Search ............... 423/144, 417, 138, 140, 423/419 R; 568/451, 909; 502/74

[56] References Cited

U.S. PATENT DOCUMENTS

| | | | |
|---|---|---|---|
| 3,810,967 | 5/1974 | Itarutakasu et al. | 423/417 |
| 3,816,337 | 6/1974 | Usami et al. | 423/417 |
| 3,855,396 | 12/1974 | Kniese et al. | 423/417 |
| 4,404,119 | 9/1983 | Lagace et al. | 423/417 |
| 4,435,517 | 3/1984 | Simons et al. | 502/74 |

OTHER PUBLICATIONS

Homogeneous Catalysis-II "New Hydroformylation Technology with Cobalt Carbonyls" Forster et al. pp. 19-26 Chapter by Kummer et al. (1973).

*Primary Examiner*—Theodore Morris
*Assistant Examiner*—Edward Squillante

[57] ABSTRACT

Cobalt is recovered from the oil/water mixed reaction product of oxonation by increasing the carbon dioxide level in the reaction product and adjusting the temperature to enhance the carbon dioxide level in the oil water phase to promote the formation of cobalt carbonate which is allowed to settle and may be removed and/or recycled increasing cobalt utilization and reducing environmental problems.

3 Claims, 1 Drawing Sheet

MINIMIZING COBALT CATALYST LOSS IN THE PRODUCTION OF ALCOHOLS BY HYDROFORMYLATION OF OLEFINS

This application is a continuation-in-part of application Ser. No. 447,881 filed Dec. 8, 1989, which was abandoned on Mar. 8, 1991.

This invention relates to the production of alcohols by hydroformylation processes and in particular the production of alcohols with cobalt catalyzed hydroformylation in which the amount of waste cobalt is reduced. This brings an economic benefit and also reduces the amount of cobalt in the waste water stream leading to significant environmental benefits.

The hydroformylation process, in general terms, is a process involving the preparation of oxygenated organic compounds by the reaction of carbon monoxide and hydrogen (synthesis gas) with carbon compounds containing olefinic unsaturation. The reaction is performed under hydroformylation conditions in the presence of a carbonylation catalyst or catalyst precursor such as dicobalt octacarbonyl, and results in the formation of a compound, e.g., an aldehyde which has one more carbon atom in its molecular structure than the feedstock. Subsequent hydrogenation of the primary product leads to higher alcohols which may be used for example for conversion into plasticizers.

Typically in higher alcohol production the feedstock for a hydroformylation process is a commercial $C_4$–$C_{12}$ olefin fraction and the desired end product is the respective $C_5$–$C_{13}$ saturated alcohol or derived mixed alcohol product, produced by hydrogenation of the aldehyde oxonation product. By virtue of the nature of the feedstock commonly available to industry, and indeed of the catalyst and reaction parameters employed, the oxonation reaction yields a range of products due to the numerous secondary reactions which take place. The main commercial products of the hydroformylation reaction are aldehydes and alcohols, with side reactions in the oxonation, demetalling and hydrogenation sections of the process system producing some 5 to 20 wt. % of high boiling materials, such as aldols, esters, ethers and acetals, by condensation, esterification and dehydration reactions.

In a conventional higher oxo alcohol process, the feedstock as described above is fed together with synthesis gas into an oxonation unit where catalytic hydroformylation takes place using, e.g., hydro cobaltcarbonyl as the active catalyst species.

After oxonation the product goes through a hydrogenation step to convert aldehydes into alcohols.

The product mixture after hydrogenation comprising the higher alcohol, the high boiling materials mentioned above and a low boiling fraction is then passed to a distillation unit where low boiling materials, high boiling materials and the desired alcohol product are separated. After hydrogenation, the product mixture is generally about 60–90 wt. % higher alcohol, 5–20 wt. % high boiling materials and 5–20 wt. % lower boiling materials. The low boiling material passing off overhead is a low value product, typically containing unreacted olefin feed and paraffins. The high boiling material usually contains dimers such as ethers and ether-alcohols (e.g., $C_{20}$ compounds in $C_{10}$ alcohol production) and trimers such as acetals (e.g., $C_{30}$ compounds in $C_{10}$ alcohol production), and heavier. Typically, there is present in the higher boiling component 0–5 wt. % alcohols, 15–25 wt. % ethers, 45–65 wt. % ether alcohols, 2–10 wt. % esters and 5–25 wt. % acetals. Although substantially alcohol free (apart from the heavy ether alcohols), it may contain a minor amount of alcohol which has not been removed in the distillation stage where the higher alcohol product of the hydroformylation process is separated. In U.S. Pat. No. 4,658,068 there is described a process for upgrading these heavy fractions to more useful alcohol.

In the production of higher alcohols cobalt catalyst is used for the reaction of the olefins with synthesis gas. After completion of the oxonation reaction the cobalt catalyst has to be removed from the reaction products and is recycled back to the feed for the oxonation reaction section.

Several technologies to remove the cobalt catalyst from the oxonation reaction products are being practiced. Examples are the oxidation of the cobalt catalyst with air/acetic acid to form cobalt acetate, thermal decobalting to form cobalt metal or treatment with dilute caustic to produce sodium cobaltcarbonyl. The last method is called the Kuhlmann catalyst cycle technology and involves two main process steps: first recovery of the sodium cobaltcarbonyl and second the regeneration of the hydro cobaltcarbonyl.

The first step of this Kuhlmann Cycle consists of high pressure decobalting in which oil soluble hydro cobaltcarbonyl is converted into the water soluble sodium cobaltcarbonyl. This is typically done at high temperature (100°–180° C.) and high pressure 180–300 barg) by thoroughly mixing the oxonation products with a dilute caustic solution. After cooling and depressuring the sodium cobaltcarbonyl water is separated from the oil, and after washing the oil with water for removal of cobalt traces, both water phases are combined and stored.

In the second step, the water soluble sodium cobaltcarbonyl is converted back into the oxonation catalyst hydro cobaltcarbonyl by acidification of the cobalt water with dilute sulfuric acid. The volatile hydro cobaltcarbonyl is stripped from the water by a countercurrent flow of absorbing gas, frequently syngas, which is subsequently passed through an absorber column to recover the hydro cobaltcarbonyl from the stripping gas.

In the first step of this decobalting, the reaction of hydro cobaltcarbonyl with caustic is the main reaction. However, a minor part of the cobalt catalyst is converted into cobalt (II) salts which cannot be recycled back to the olefin feed stream and is lost via the acidic waste water stream into the environment. In the conventional Kuhlmann technology, the possibilities of excessive precipitation of these cobalt salts are deliberately minimized by maintaining a low partial pressure of carbon dioxide in the oxo off-gas streams and by avoiding large excesses of caustic. This avoids solids formation and plugging of the process piping and control valves. Furthermore, by avoiding major water holdups and maximizing fluid velocities, solids settling is prevented. This leaves the cobalt salts mainly dissolved in the water stream, which is then acidified and stripped to produce a cobalt containing acidic waste water stream. Typically the waste water contains 60–200 ppm of cobalt.

In a typical industrial process, cobalt losses via this waste water stream are significant (15–30 kg/Co/day), and cause environmental problems. An end-of-pipe treatment process, which changes the pH of the water from acidic to alkaline by caustic addition, has been developed so that the cobalt hydroxide is formed and is removed from the water by flocculation and centrifuging. This process, although effective, is very costly; it requires significant investment, high operating cost and a lot of operator attention.

We have now developed a process which effectively removes cobalt salts, such as cobalt carbonate and cobalt hydroxide, from the aqueous sodium cobaltcarbonyl stream prior to contacting with sulfuric acid and stripping, without incurring additional cobalt losses or experiencing operating problems. This is accomplished by precipitation of solid cobalt carbonate with carbon dioxide which is then settled and filtered from the sodium cobaltcarbonyl water stream.

The invention leads to an acidic waste water stream of reduced volume containing cobalt species generally below 20 ppm Co, and does not require further expensive end-of-pipe treatment for cobalt removal. Furthermore the invention produces cobalt solids, which can be recycled back to the oxonation section via the catalyst makeup step.

The present invention therefore provides a process for the recovery of cobalt from the oil/water mixed reaction product of oxonation by increasing the carbon dioxide level in the reaction product and adjusting the temperature of the caustic treated oxo product to enhance the carbon dioxide level in the oil water phase which results from such caustic treatment of the oxonation reaction product to promote the formation of cobalt (II) carbonate and allowing the cobalt (II) carbonate to settle for removal.

The caustic treatment of the crude oxonation reaction product is carried out using 9–15 wt. % (relative to the weight of crude oxonation product) of a dilute aqueous caustic (NaOH) solution containing from about 3–5 wt. % of NaOH.

The temperature of the caustic treated oxo product is lowered from the typical 140°–160° C. to about 30°–50° C. in accordance with the present invention by cooling using a cooling water heat exchanger. Due to the cooling in the presence of high pressure offgas, the $CO_2$ tends to dissolve in the liquid phase. The carbonate concentration is effectively enhanced thereby promoting the precipitation of cobalt (II) carbonate.

The process is applicable to the production of alcohols from any olefins which may be subjected to hydroformylation, but is particularly suited to the hydroformylation of $C_4$ to $C_{16}$, preferably $C_4$ to $C_{12}$ olefins for the production of $C_5$ to $C_{13}$ alcohols.

Conventional hydroformylation conditions may be used in the process of this invention and the operating temperatures, pressures and other conditions, such as synthesis gas composition, may be controlled in accordance with the usual expertise of the person skilled in the art to maximize yield of the desired higher alcohol product. For example, the hydroformylation reaction may be carried out at a pressure of 150–300 atm, and a temperature of from 120° C. -190° C.

The catalyst may be used in desired active form for example in a concentration of from 0.05-3 wt. % preferably 0.05 and 1 wt. % as metal based on the olefinic feed. Typically the synthesis gas used might have a H2:CO volume ration in the range 0.9:1-1.5:1.

The cobalt separation technique of the invention may conveniently be divided into four subsections: (i) Precipitation of cobalt salts (ii) Settling of cobalt salts (iii) Physical separation of the cobalt salts (iv) Recycle of recovered cobalt salts. Cobalt salts are defined as a mixture of mainly cobalt (II) carbonate, cobalt (II) hydroxide and a minor amount of cobalt metal.

Figure 1:
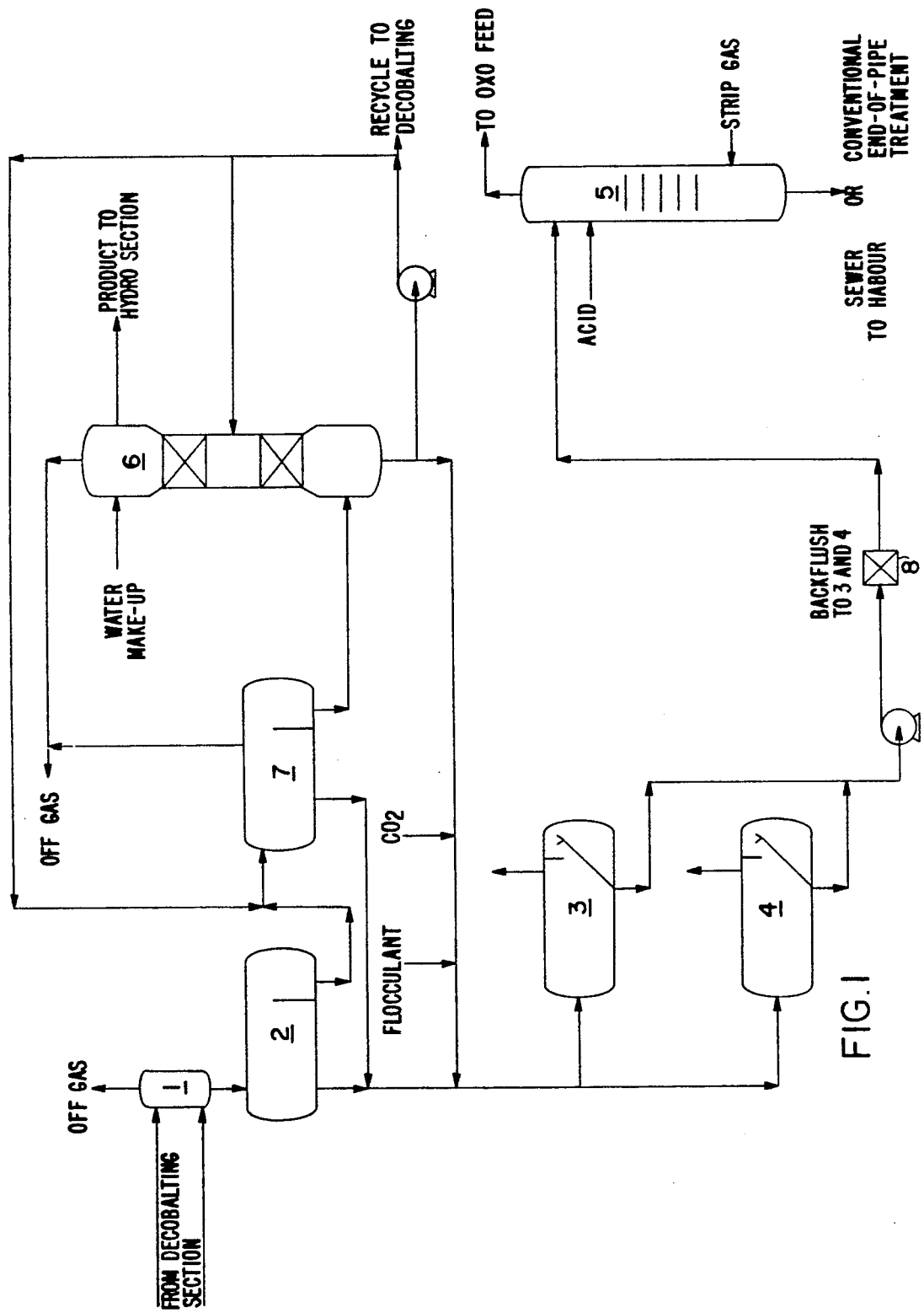
FIG. 1 is a flow diagram illustrating the operation of the process in a typical hydroformylation facility.

The process is illustrated by reference to FIG. 1 in which oxo product and dilute caustic containing sodium cobaltcarbonyl are coming from the decobalting section and flow into low pressure gas-liquid separator 1. The liquids from separator 1 flow into water-oxo product separator 2. The separated oxo product is mixed with recycled wash water from tower 6 and sent to a second water-oxo product separator 7.

It is critical to the process of this invention that the pH of the water leaving the decobalting section be maintained between 6.5 and 9.0, preferably from 8.0 to 8.5, otherwise the process is ineffective. At pH values below 6.5, the process cannot remove cobalt (II) from solution, and at pH values above 9.0, cobalt hydroxide will be formed instead of the desired cobalt (II) carbonate.

The oxo product from separator 7 is fed to wash tower 6, while the water phase is combined with the one from separator 3 and sent to settlers 3 and 4.

In wash tower 6 the oxo product is water washed and after separation sent to hydrogenation. The wash water from tower 6 bottoms is partly recycled over tower 6 itself, partly sent to separator 7, while the remaining goes to settlers 3 and 4.

In settlers 3 and 4 entrained oxo product and solids are separated from the sodium cobalt carbonyl water, which is pumped through cobalt solids filter 8 to stripper column 5. The cobalt solids which build up in filter 8 are regularly backflushed into settlers 3 and 4.

In stripper column 5 acid is added to the sodium cobaltcarbonyl water and is countercurrently stripped with gas. This stripgas containing hydro cobaltcarbonyl is contacted with oxo feed to recycle the cobalt catalyst back to oxonation. The stripped water from column 5 is sent to conventional end-of-pipe treatment or to a sewer.

Details of the cobalt separation technique (i) Precipitation of Cobalt Salt

The presence of carbon dioxide in the high pressure oxo offgas promotes the formation of cobaltcarbonate. This is accomplished by leaving 1–3 volume % carbon dioxide in the fresh synthesis gas as opposed to earlier processes when carbon dioxide has been deliberately removed (to levels of less than 0.1% by volume) from the syn-gas feed, the carbon dioxide level may be further enhanced by recycling hydrogen containing 10–15 volume % carbon dioxide to the oxonation section. This is contrasted to prior art practice where such recycled gas contained less than 0.1% volume of $CO_2$. We have found that contrary to the general belief, the presence of excess carbon dioxide is not harmful to the oxonation process and does not create additional cobalt losses. To facilitate the formation of cobalt hydroxide, an excess of caustic may be injected into the decobalting section in order to reach a preferred pH of 8–8.5 in the water leaving the decobalting section.

An alternative is to use fresh synthesis gas free of carbon dioxide, and to recycle hydrogen containing 10-15 volume % carbon dioxide to the oxonation section.

Cobalt carbonate is less water soluble than cobalt hydroxide, therefore the presence of carbon dioxide in the high pressure oxo offgas is more effective in removing water soluble cobalt (II) species than the addition of excessive amounts of caustic.

To maximize the cobaltcarbonyl recovery the oxo product is washed with a water stream in a wash tower 6. Carbon dioxide may then be injected into the water stream preferably as it leaves the wash tower and passing to the cobalt water storage drums 3 and 4 to further promote the formation of cobalt carbonate. A flocculant, for instance a poly methyl methacrylate, may be injected to facilitate the cobalt carbonate particle growth and the settling in the cobalt water storage drums. Another method of stimulating cobalt carbonate particle growth is the recycle of wash tower 6 bottoms water back to the decobalters or to the product settlers 2 and 7, since the cobalt species present in this recycle stream enhance the formation of larger cobalt carbonate particles.

(ii) Settling of Cobalt Salts

The addition of a flocculant to sodium cobaltcarbonyl water steams helps the settling of the cobalt carbonate and is not harmful to the subsequent volatilization step in stripper column 5. The flocculant does not cause foaming or other process problems during the stripping of the acidified water stream.

After the formation of the cobalt salts as much as possible of the solids shall be allowed to settle from the sodium cobalt carbonyl water stream prior to pumping it to the stripper column 5. This may be accomplished by leading the water from the product separation step to the two parallel and/or run in series settlers 3 and 4, which also act as sodium cobalt carbonyl water storage drums. These two drums are designed for maximum settling performance by creating a residence time of 5-10 hours. Internals, such as floating suctions, may be installed to prevent cobalt particles entraining from the drums and to avoid stirring up of the already settled particles. Another important aspect of maximizing settling times is the reduction of the water flows entering the settlers. This may be achieved by minimising the net water flow going to the wash column 6, which also proceeds via partly recycling over wash column 6 itself. The wash bottoms stream is also used for prewashing the oxo product going to the oxo product separator 7.

(iii) Physical Separation of Cobalt Salts

The settled water containing sodium cobaltcarbonyl is pumped from settlers 3 and 4 to the volatilization column 5 to liberate hydro cobaltcarbonyl. To minimize the risk of cobalt salts entering this tower, the water stream is preferably first passed through filter 8 to remove any entrained solids. The flush water from the filter is sent back to the settler drums. An important aspect of filter operation is the stability of the water flow to the volatilization tower 5, which is not affected by the filter operation.

An alternate way of removing entrained cobalt particles is to pass the water stream via a centrifuge, while avoiding air contact to prevent oxidation of the cobalt carbonyls. The addition of a flocculant is required for centrifuging, but does not harm the volatilization operation.

(iv) Recycle of Cobalt Sludge

The cobalt salts, which settle out in the drums 3 and 4, build up as sludge and require periodical removal. During this removal the watery sludge is centrifuged or filtered to concentrate the sludge, the water with sodium cobalt carbonyl is fed back to the process.

The recovered cobalt salts, mainly cobalt carbonate, can be recycled back to the oxonation process as make up catalyst. This is done via the conventional process route by returning it to the cobalt supplier, who reworks it into cobalt oxide. Another method of recycling is to first wash the sludge with a carbon dioxide and/or carbonate containing water stream to remove sodium salts from the sludge and then pump it to the so-called preforming reactors to convert cobalt carbonate into hydro cobaltcarbonyl. Normally these reactors preform cobalt oxide into hydro cobaltcarbonyl. The recycle of the cobalt sludge would not be possible in the conventional process, since caustic treatment of the acidic waste water stream leads to the formation of a mixture of cobalt hydroxide/sulphate, which is very difficult to convert into hydro cobaltcarbonyl.

The process described above has led to a significant reduction of the cobalt losses into the acidic waste water stream. Historically they have been in the order of 15-30 kg Co/day (based on a monthly average), while after implementation of the invention they have been reduced to below 7-8 kg Co/day. In the meantime the average cobalt circulation rate has been increased from 30 kg Co/hr to 100 kg Co/hr, which would otherwise have caused a significant increase of cobalt losses.

EXAMPLE 1

In this example the role of carbon dioxide on the cobalt removal process is demonstrated.

At the start of the experiment, the oxonation unit was operated with a synthesis gas stream free of carbon dioxide, while no hydrogen containing 10-15 volume % carbon dioxide was recycled to the oxo section. A fairly high proportion of the cobalt (II) remaining dissolved in the liquid going via filter 8 to stripping column 5. Although cobalt circulation rate was low (30 kg/hr) typically 10 kg Co/day were lost to the sewer.

By addition of carbon dioxide to the fresh synthesis gas (about 2 volume %), cobalt losses dropped to 7 kg Co/day. Start-up of the recycle compressor and feeding hydrogen/carbon dioxide reduced the losses even further down to 6 kg Co/day.

In another comparative example, the fresh syngas was left free of carbon dioxide, but by recycling hydrogen/carbon dioxide the cobalt losses were reduced in the same manner down to 6 kg Co/day.

EXAMPLE 2

This example shows the effectiveness of the filter in removing solids from the water stream which is fed to stripping column 5.

Using the process of Example 1, liquid was pumped from drum 4 to column 5, while by-passing filter 8. Under these circumstances, a constant 10-12 kg Co/day was lost to the environment via the sewer. These losses could not be attributed to malperformance of stripping column 5.

Without changing any of the operating parameters, filter 8 was taken in service with the backflush liquid of the filter 8 going to drum 3. In the improved operation losses decreased to an average of 6-8 kg Co/day, which demonstrates that the filter is capable of removing 4-6 kg/day cobalt solids from the aqueous feed going to column 5.

At a lower cobalt circulation than above, the same test was repeated. Without the filter, 5 kg Co/day emitted via the discharge of column 5, startup of the filter reduced the losses down to 2-3 kg Co/day.

EXAMPLE 3

This example illustrates the chemical composition of the oil/water mixture from which cobalt is recovered in accordance with this invention.

| Oil/Water Mixture: | 10-20% wt. water, preferably about 15% |
|---|---|
| Oil Phase: | |
| (A) Olefin/Paraffins | 10-15 wt. % |
| (B) Aldehydes/Alcohol/Formate Esters | 70-80 wt. % |
| (C) Heavy Fractions | 10-15 wt. % |
| Component (B) of the Oil Phase: | |
| Aldehyde: | 20-50 wt. % |
| Formate Esters: | 10-15 wt. % |
| Alcohol: | Balance (10-50 wt. %) |
| Total | 70-80 wt. % |

We claim:

1. In the process of conducting cobalt catalyzed hydroformylation of olefins to form a hydroformylation product in a hydroformylation reactor, the catalyst being hydro cobalt carbonyl, comprising the stages of hydroformylation, hydrogenation, decobalting of the hydro cobalt carbonyl catalyst by conversion of said catalyst to water soluble sodium cobalt carbonyl by treatment of the hydroformylation reaction product with a dilute aqueous caustic solution to produce a solution containing water soluble sodium cobalt carbonyl, which solution is subsequently is acidified to produce volatile hydro cobalt carbonyl, said solution also containing dissolved cobalt (II) salts which cannot be converted to hydro cobalt carbonyl, said solution being subsequently separated into hydroformylation product and water phase, the improvement which comprises employing in said hydroformylation (a) hydroformylation synthesis gas containing 1-3 volume % carbon dioxide, (b) recycling hydrogen containing 10-15 volume % carbon dioxide into said hydroformylation reactor, (c) maintaining the temperature of the dilute caustic treated hydroformylation product at about 30°-50° C., and (d) maintaining the pH of said water phase produced subsequent to said decobalting stage at 6.5 to 9.0, forming cobalt (II) carbonate and allowing said cobalt (II) carbonate to settle for removal from said aqueous phase of said cobalt (II) carbonate.

2. The process of claim 1 in which the olefins are $C_4$ to $C_{16}$ branched or linear olefins.

3. The process of claim 1 wherein the hydroformylation product is washed with water and carbon dioxide is injected into the wash water.

* * * * *